(12) United States Patent
Tanaka

(10) Patent No.: US 10,543,067 B2
(45) Date of Patent: Jan. 28, 2020

(54) METHOD, SYSTEM, AND KIT FOR COLORING DENTAL CERAMICS

(71) Applicant: Asami Tanaka, Skokie, IL (US)

(72) Inventor: Asami Tanaka, Skokie, IL (US)

(73) Assignee: Tanaka Dental Products, Skokie, IL (US)

( * ) Notice: Subject to any disclaimer, the term of this patent is extended or adjusted under 35 U.S.C. 154(b) by 0 days.

(21) Appl. No.: 15/902,049

(22) Filed: Feb. 22, 2018

(65) Prior Publication Data

US 2019/0254788 A1  Aug. 22, 2019

(51) Int. Cl.
| | | |
|---|---|---|
| *A61K 6/00* | (2006.01) | |
| *A61C 13/08* | (2006.01) | |
| *C04B 41/46* | (2006.01) | |
| *A61K 6/02* | (2006.01) | |
| *C04B 41/82* | (2006.01) | |

(52) U.S. Cl.
CPC .......... *A61C 13/082* (2013.01); *A61K 6/0058* (2013.01); *A61K 6/02* (2013.01); *C04B 41/46* (2013.01); *C04B 41/82* (2013.01)

(58) Field of Classification Search
CPC .. A61C 13/083; A61C 8/0012; A61K 6/0002; C04B 41/86
See application file for complete search history.

(56) References Cited

U.S. PATENT DOCUMENTS

| | | | | |
|---|---|---|---|---|
| 6,365,132 B1* | 4/2002 | Litkowski | ................ | A61K 8/25 424/49 |
| 8,277,783 B2* | 10/2012 | Creamer | ............... | C01B 15/047 424/53 |
| 8,491,874 B2* | 7/2013 | Creamer | ............... | C01B 15/047 424/49 |
| 2007/0141537 A1* | 6/2007 | Ibsen | ................... | A61C 13/225 433/226 |
| 2011/0306017 A1* | 12/2011 | Tanaka | ................. | A61C 13/082 433/203.1 |
| 2014/0300014 A1* | 10/2014 | Tanaka | ................. | A61C 13/082 264/20 |

OTHER PUBLICATIONS

Protocols for Predicatable Aesthetic Dental Restorations, Irfan Ahmad (No date).*
Optimizing Your Shade-Matching Success (Sep. 2015).*

* cited by examiner

*Primary Examiner* — Eisa B Elhilo

(57) ABSTRACT

A system, method and kit for coloring dental ceramics. The system, method, and kit resulting capable of adjusting the shade of a dental restoration milled from a colored zirconia porcelain block from one color value of the VITA shade guide to a different color value of the VITA shade guide.

14 Claims, 2 Drawing Sheets

METHOD, SYSTEM, AND KIT FOR COLORING DENTAL CERAMICS

BACKGROUND

Often during sporting, automobile accidents, or due to illness or disease, individuals may lose one or more teeth. The loss of teeth may result in loss of integrity of the bite. Also, many individuals are uncomfortable with the appearance of missing teeth. The dental arts have established technology to create artificial teeth that mimic an individual's original teeth. For example, the dental arts, using ceramics, can mold teeth that look mimic natural teeth.

Among others, zirconia is a popular material from which dental replacements are made. However, zirconia creates a very hard surface which is not easily colored. Zirconia also requires firing at temperatures over 900° C. At that temperature, the pigments traditionally used to color dental ceramics disappear and lose color. Presently it is the knowledge of that art that no stains or other colorants will adhere or bond to Zirconium ceramics.

Zirconia is a very strong material and the dental sciences are quickly adopting zirconia ceramics for use in dental restorations. However, a drawback to the use of zirconia is the stark white color of the material. Most individuals prefer dental restorations which have the appearance and color of a natural tooth. Specifically, individuals wish to have dental restorations that blend in naturally with the remaining teeth.

BRIEF SUMMARY

A system, method and composition for coloring dental ceramics. The system, method, and composition resulting in natural color matching by shifting the color of a dental ceramic made from a pre-shaded zirconia block with increased efficiency and reduced preparation time.

DETAILED DESCRIPTION

Figure 1:
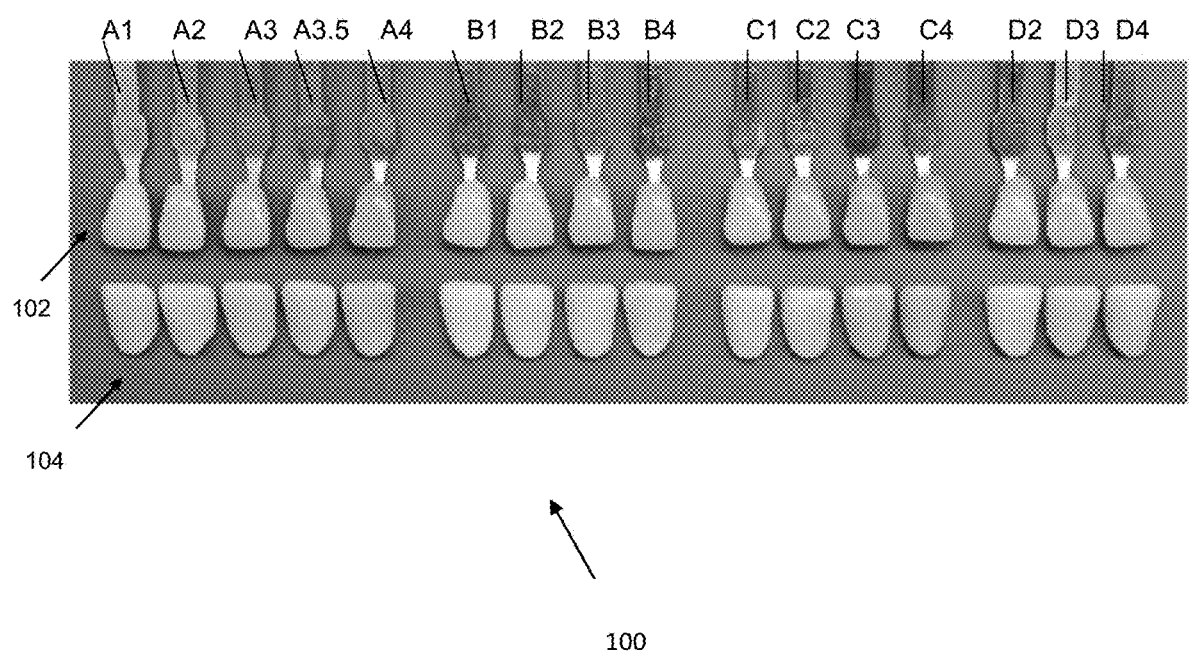
FIG. 1 illustrates the range of natural colors achieved with the disclosed system, method, and composition.

Dental restoration after tooth loss is quite popular to improve the visible appearance of the face and also to restore the integrity of the bite. Individuals who have suffered tooth loss may want their restorations to have a natural appearance and match in size, shape, and color, their natural teeth. Aesthetically pleasing replacements are increasingly sought after.

Technologies, such as CAD/CAM technology may be used in dentistry to help dentists and dental technicians fabricate precise shapes and sizes for dental restorations, including, for example, inlays, onlays, crowns, and bridges. Dentists may use CAD/CAM and other related technologies to provide their patients with durable, well-fitted single and multiple tooth restorations.

Dentists and dental technicians may use CAD/CAM and other technologies to design the anatomical features, size, and shape of a tooth restoration, for example but not limited to, on a computer. For example, with CAD/CAM, the machine fabricates the restoration through a milling chamber that crafts the tooth-like ceramic material into a precise replica of the drawing.

There are many different materials used for making dental restorations. Among them, ceramic may be used for in-lays, on-lays, crowns, veneers, as well as full restorations, among others. For example, full ceramic restorations are particularly desirable because their color and translucency mimic natural tooth enamel.

Computerized dentistry, such as by the use of CAD/Cam technology, has enabled the application of zirconium-oxid ($ZrO_2$). The introduction of this zirconia in restorative and prosthetic dentistry may have encouraged the use of full ceramics without limitation. With the exception of zirconium-oxide, existing ceramics systems may lack reliable potential for the various indications for bridges without size limitations. Zirconium-oxide with its high strength and comparatively higher fracture toughness may be more reliable than existing ceramic systems. With a three-point bending strength exceeding 900 megapascals, zirconium-oxide may be used in virtually every full ceramic prosthetic solution, including bridges, implant supra structures and root dowel pins.

As technology improves, more stringent requirements are being placed on the aesthetics of teeth. Metals and porcelain may currently be the materials of choice for crowns and bridges. The demand for full ceramic solutions, however, continues to grow. Consequently, industry and science are increasingly compelled to develop full ceramic systems. In introducing full ceramic restorations, such as base structures made of sintered ceramics, more attention must be focused on developing a coloring system that improves the natural appearance of the ceramics.

The super hard surface that makes zirconia appealing for ceramic restorations, does not lend itself to easy coloration. Disclosed herein is a method, system, and composition that may be used to impart a natural color to dental restorations. The method, system, and device may eliminate the need to use mask layers of opaque and body porcelains. The method, system, and solution may be capable of preparation on the edge of a knife and may eliminate the need to shoulder prep for color.

Additionally, the method, system, and composition may require short or no drying time and multiple applications of different shades may be possible. Application of the method, system, and composition may result in a three dimensional appearance of the dental restoration.

Dental restorations are commonly prepared with a substructure of a metal or ceramic material upon which substructure layers of porcelain are applied. For example, ceramic or metal alloy substructures may be first covered by an opaque layer, followed by an opacious dentin layer, a dentin layer and finally an incisal porcelain layer.

Aesthetics of the dental restoration is of great importance. Patients desire a natural appearance of the prosthesis. In order to achieve a natural appearance of the prosthesis, the dental technician must carefully match and color the framework or facing ceramics. A natural appearance relies not only on color, but on translucence. Currently, most coloring systems require several procedures and layers which are finally fired (sintered) in an oven. The current coloring systems are therefore time consuming and expensive. Additionally, the current coloring systems may not provide a satisfactory level of natural appearance. For example, dental implants created under current coloring systems often have a shadow from the cast metal. Increased numbers of ceramic layers may be used to mask the shadow from the cast metal, however, to accommodate the increased number of layers, the dental professional must remove an equivalent amount of tooth material. The removal of tooth material, for example, removal of enamel that compromises the integrity of the dentine layer, has lead to the observation that over 22% of restored teeth decay after 5 years.

We disclose herein a dental restoration color system that allows for a natural tooth color result with less preparation time, increased color stability upon firing, and requiring less material therefore less invasive tooth preparation.

The disclosed system is particularly applicable to zirconium restorations. Zirconium restorations provide increased strength and better fit while also having excellent biological compatibility, which may prevent or reduce gum erosion.

There are several industry standards including shade guides such as VITA® (made by VITA Zahnfabrik). For the purpose of this application, reference is made to the VITA® shades as a shade guide. VITA® shades for teeth are used for making dental prostheses with various color hues. The density of the color present for each hue is classified on a numerical scale with lower numbers indicating less color density and higher numbers indicating higher color density. Therefore, "VITA" herein means the VITA CLASSICAL A1-D4® shade guide. See FIG. 1, 100 for a visual example of the VITA shade guide. The VITA shade guide includes a series of colors that are given reference numerals for identification of the color of the natural dentition. The series of reference numerals are: A1, A2, A3, A3.5, A4, B1, B2, B3, B4, C1, C2, C3, C4, D2, D3, D4, Incisal Light, Incisal Dark, Occlusal, and Pink. See FIG. 1.

The liquid compositions of the system, method, and kit may be formulated to dry quickly and do not require preheating prior to sintering. The liquid compositions of the system, method, and kit may be applied by dipping or may be applied by brushing, spraying, or any known way of applying. Application of the liquid composition by brushing may allow for the application of different shades both inside and outside of the restoration.

Dental restoration materials may be provided in blocks of material, for example, dental zirconia ceramic blocks. Dental equipment, such as the CAD/Cam technology, may be used to mill the solid blocks of the restoration material, such as zirconia ceramic, into a dental restoration such as but not limited to a bridge, tooth, cap, or other structure.

CAD/CAM restorations may be milled from solid blocks of white composite resin or may be made from porcelain matching the shade of the restored tooth.

CAD/CAM restorations may be milled from solid blocks of colored composite resin or may be made from porcelain. For example, zirconia porcelain blocks (also referred to as blanks and/or colored blanks) are available in monochrome, in the 16 VITA classic shades, in multicolor, and in various different color gradients. Colored blanks may be used to increase the efficiency of creating a restoration. For example, the colored blanks may eliminate one or more shading steps, as discussed in more detail below. The method, system, and kit disclosed herein is particularly useful for the shading of blocks or blanks that are provided as colored blanks. Starting with a colored blank, in most cases, does not eliminate all of the shading steps. Matching the coloration of a patients teeth in order to obtain an aesthetically desirable restoration usually requires additionally shading to reach the desired color. Therefore, even when a colored blank is used, there are still additionally shading steps. We disclose a system, method, and kit for increasing the efficiency of achieving desired shades when using colored blanks.

As discussed above, porcelain blanks, e.g., zirconia porcelain blanks are available in monochromatic as well as multicolor options. For example, blanks are available in every single color of the VITA shade guide, among others. All together, there are at least sixteen shade options available. In addition, each shade is available in various thicknesses, e.g., 10 mm, 12 mm, 14 mm, 16 mm, 18 mm, 20 mm, 22 mm, 24 mm, and so on. Considering that there are at least sixteen shade options and there are several different thicknesses, one can immediately envision the size of inventory that must be maintained. A manufacturer, dental laboratory, or similar provider, will have to dedicate considerable storage space to the large inventory of blanks to ensure that it has the appropriate materials for the large dental variety of its customers and patients. We disclose a method, system, and coloring kit that reduces the size of inventory that is necessary when implementing colored blanks.

Our methods, system, and coloring kit is capable of quickly, often with one application, adjusting the color of a colored blank from one color of the VITA shade guide to a different color of the VITA shade guide. For example, one may decide to stock only the A1 shade or the A2 shade, as these are popular. Using our method, system, and kit a dental restoration produced out of an A1 shade block can be easily, quickly, and reliably adjusted to the A3 shade. In another example, one may start with an A2 shade block. Using our method, system, and kit a dental restoration produced out of an A2 shade block can be easily, quickly, and reliably adjusted to any other desired shade, including but not limited to, A3, A4, B, C, and etc. In other words, rather than having to mix various colors and guess at how to bring the color of the block from A2 to A4, the technician merely applies the coloring material designated "A2 to A4" and the color is reliably achieved. There is no trial and error. This is an instant result of the exactly desired color adjustment.

The system, method, and kit includes several benefits. Among them, it increases efficiency by drying instantly which allows a zirconia dental object to be sintered with minimal (approximately ten seconds and less than one minute) of wait time. The results are consistent, an accurate predictable shade may be achieved. There are less blanks to stock because a single blank can be used for many shades by using the kit.

We disclose a system, method, and kit that includes several color solutions. Each color solution is formulated to easily, quickly, and reliably adjust the color of a restoration from one value of the VITA shade guide to a different value of the VITA shade guide. The method, system, and kit has the advantage of providing a solution to the laboratory that allows it to acquire the benefits of using a colored block (e.g., reduction of time and increased restoration quality) while also reducing the storage space requirements inherent in maintaining the colored blocks in the laboratory.

Using our method, system, and kit, the provider (e.g., the laboratory, manufacturer, or other provider) may maintain a limited number of colored blanks. The disclosed system, method, and kit allows the provider to mill and change the shade of the colored blank from one value on the VITA shade guide, to a different color on the VITA shade guide with increased efficiency over those methods known in the art. The disclosed method, system, and kit achieves increased efficiency and decreased time for shade adjustment while also having other advantages. For example, the method, system, and kit includes various shading materials (which may be liquids or may be powders or other concentrates that require dilution before use). Common color liquids include acids, which may have the effect of oxidizing fingers and instruments. Other color liquids have water base which is popular in the marks but does not quickly penetrate the restoration. For example, water based coloring liquids take 10-20 minutes or more to penetrate the restoration. The need for multiple applications of the shade, interspersed with 10-20 minute or more drying periods means that there is typically hours of waiting before the restoration can be fired. For example, with the disclosed method, system, and kit it takes only about 5 seconds to apply the color materials (e.g., by dipping, brushing, spraying, or otherwise) to the restoration and about 5 seconds to remove the excess from the restoration and then after only about 10 seconds, the restoration is ready to fire. This is a considerable surprising and highly significant reduction in preparation time. The preparation time is decreased by at least a factor of sixty. The method, system, and kit provides a color adjustment from a precolored block that reduces the time between color adjustment and firing by a factor of about ten, about twenty, about thirty, about forty, about fifty, about sixty, about seventy, about eighty, about ninety, about one-hundred, about ten to about one hundred or more when compared to methods known in the art.

The disclosed system, method, and kit also produces increased efficiency by reducing the time spent changing blocks in the milling machine. It is a clinical reality that each patient's natural teeth have a unique shade. Most dental laboratories servicing such clients therefore desire to have a range of shade blocks in stock, e.g., VITA A1, A2, A3, or any or all of the sixteen shades, available to use depending on the clinical requirements. Each time that the laboratory is required to change the block in the milling machine, it takes time. For example, if an A2 block is desired but an A1 block is currently in the milling machine, the laboratory technician must take the time to change the block. Using the disclosed system, method, and kit, the laboratory may not have the need of changing the block in the milling machine for each client's unique needs. For example, if an A1 block is in the machine and an A3 block is desired, the technician can mill the restoration out of the A1 block and then apply the A1 to A3 adjustment liquid to achieve the desired shade. This shade adjustment in full is possible in less than one minute and therefore allows an instant adjustment with time savings at multiple steps in the system.

We disclose a method, system, and kit which is made from a hydrocarbon liquid that quickly absorbs and therefore significantly reduces the time that it takes to adjust a restoration before it is fired.

An exemplary conventional method of preparing restorations involves taking an image of the defective tooth area. This image may be used to draw the data into a computer and proprietary software may be used to create a virtual restoration. The software may then send this virtual data to a milling chamber where the dental restoration is carved out of a solid block (e.g., a blank) of, for example, composite resin or porcelain. The resultant restoration can then be adjusted in the patient's mouth and bonded in place.

If porcelain is used, practitioners may treat the restoration with stains and glazes and subsequent heat treatments to both beautify and strengthen the definitive restoration prior to bonding. Practitioners may perform acid etching of both the underside of the restoration and the topside of the tooth itself, which may microscopically increases surface area on both opposing surfaces. Practitioners may then use composite resin materials to fuse the resultant restoration to the tooth, completing the restoration process.

Currently, using available methods, staining and glazing to match the patient's natural tooth color is a complicated and time consuming process. For example, in order to achieve a natural appearance of the restoration, the tooth color and the translucence must be simulated over several layers. For example, practitioners may use intermediate layers such as dye pastes or dye suspensions, which may require several applications, each application requiring and individual setting and drying time. After several procedures, the restoration may be fired in an oven. This process is time- and cost-intensive.

To reduce the amount of time, CAD/CAM restorations may be milled from solid blocks of colored composite resin or may be made from porcelain. For example, zirconia porcelain blocks (also referred to as blanks) are available in white, monochrome, in the 16 VITA classic shades, in multicolor, and in various different color gradients. Colored blanks may be used to increase the efficiency of creating a restoration. For example, the colored blanks may eliminate one or more shading steps. Starting with a colored blank, in most cases, does not eliminate all of the shading steps. Matching the coloration of a patients teeth in order to obtain an aesthetically desirable restoration usually requires additionally shading to reach the desired color. Therefore, even when a colored blank is used, there are still additional shading steps. Conventional color liquids take 10-20 minutes or more to penetrate the restoration. The need for multiple applications of the shade, interspersed with 10-20 minute or more drying periods means that there is typically hours of waiting before the restoration can be fired.

We disclose a system, method, and kit for increasing the efficiency of achieving desired shades when using colored blanks.

The formulation of the disclosed system, method, and kit of compositions that provide a unique and surprising feature of reliably adjusting the color from one VITA reference color to a different VITA reference color while requiring no drying time between layers.

The disclosed technology may enable the dentist, dental technician, or ceramist to reproduce the subtleties of natural dentition, for example, matching a zirconia crown to a natural root. Furthermore, the technology may disguise opacity, and may enhance translucency, and may provide subtle characterization for a natural looking result.

A first method of using the system may be as follows. However, other methods are foreseen, therefore the following is a non-limiting description of one method of using the system.

1. Prepare the Zirconia Surface

Dust may be removed from the pre-sintered zirconia crown. For example, dust may be completely removed from the zirconia crown, especially the inside incisal and angle regions. A firm bristled brush, for example but not limited to a CLEANUP BRUSH may be used to remove the dust.

Mark the regions to be stained, for example, the cervical, body, and incisal. Marking may be made on the surface of the zirconia, for example, using a graphite pencil. The marks may disappear during firing.

2. Select your Colors

Choose coloring liquids suitable for the areas to be shaded. In one example, both the outer and inner surfaces of a zirconia understructure may be treated which may produce a translucent effect. In another example, when restoring discolored teeth, inner surfaces may not be stained which may help retain the original opacity of the zirconia.

Colors may be chosen by using a color guide which may be included, for example, with a kit of the system. In one example, the liquid compositions may be formulated to match the shades of, for example but not limited to, the VITA CLASSIC SHADE GUIDE.

3. Apply Colors

Each color liquid of the system may be shaken well before using. One may apply the color using an applicator brush. The applicator brush may be dipped into the liquid of the system and any excess color may be removed against the edge of the bottle.

The dipping and painting with the disclosed liquid may be effective after a 5 second application and subsequent layers may be applied with no drying time in between. The disclosed colorant may penetrate through a 3 mm or larger sample with no preheating required. After application of the disclosed colorant, the restoration, such as a Zirconia restoration, may be sintered in an oven at a temperature of approximately 1450° C. to approximately 1550° C.

A second method of using the system, method, and kit may be as follows. However, other methods are foreseen, therefore the following is a non-limiting description of one method of using the system.

Dust may be removed from the pre-sintered zirconia crown made from a colored zirconia blank. For example, dust may be completely removed from the zirconia crown. A firm bristled brush, for example but not limited to a CLEANUP BRUSH may be used to remove the dust.

2. Choose Color

Colors may be chosen by using a color guide which may be included, for example, with a kit of the system. In one example, the liquid compositions may be formulated to match the shades of, for example but not limited to, the VITA CLASSIC SHADE GUIDE. As a non-limiting example, a pre-sintered zirconia crown may be made from an A2 colored zirconia blank. A color adjustment from A2 to A3 may be desired. One would therefore choose the coloring liquid designated "A2 to A3."

3. Apply Colors

Each color liquid of the system may be shaken well before using. One may apply the color by dipping. The system, method, and kit is capable of affecting the desired color adjustment during a dipping session of approximately five (5) to approximately ten (10) seconds. If desired, one may of course apply the color in other manners, e.g., by using an applicator brush. The applicator brush may be dipped into the liquid of the system and any excess color may be removed against the edge of the bottle. However, for the sake of efficiency, the system, method, and kit was designed to provide a color adjustment in approximately five to approximately ten seconds of dipping. The excess color may be removed as known in the art in approximately five to ten seconds. With optimal usage, the system, method, and kit provides a shade adjustment in approximately ten seconds.

In a variation, the dipping and painting with the disclosed method, system, and kit may be effective after a 5 second application and subsequent layers may be applied with no drying time in between. The disclosed colorant may penetrate through a 3 mm or larger sample with no preheating required. After application of the disclosed colorant, the restoration, such as a Zirconia restoration, may be sintered in an oven at a temperature of approximately 1450° C. to approximately 1550° C.

This coloration process removes the guesswork out of coloration. The technician does not have to wait a long time for drying to discover if the desired shade has been reached. The highly efficient method which is faster and more efficiency that currently known methods. This is a considerable surprising and highly significant reduction in preparation time. The preparation time may be decreased by a factor of sixty. The method, system, and kit provides a color adjustment from a precolored block that reduces the time between color adjustment and firing by a factor of about ten, about twenty, about thirty, about forty, about fifty, about sixty, about seventy, about eighty, about ninety, about one-hundred, about ten to about one hundred or more when compared to methods known in the art.

Process

Technical Specifications

Figure 2:
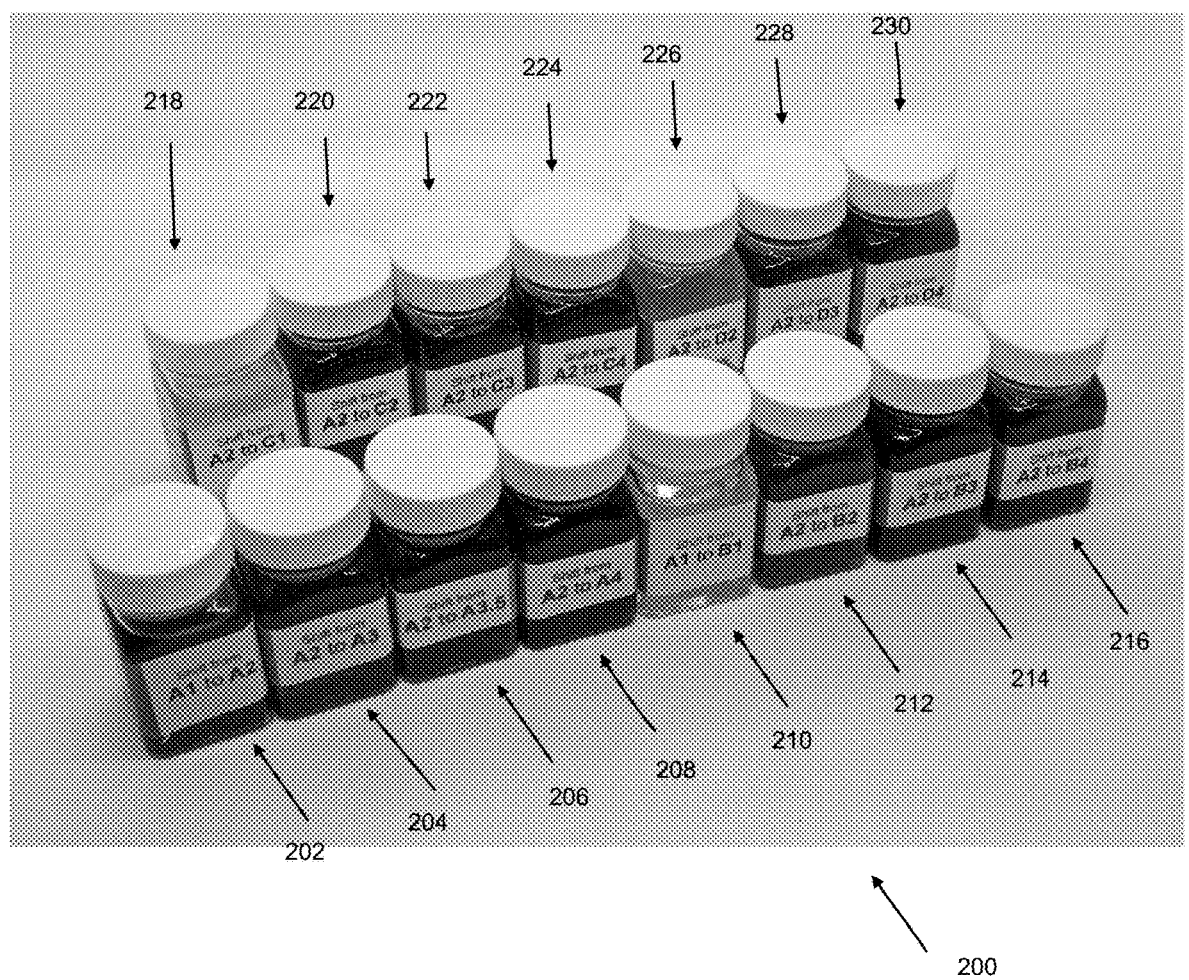
FIG. 2 illustrates a kit.

The method, system, and kit may be provided as a kit containing multiple ready to use liquids. Turning to FIG. 2, we see an exemplary kit 200 containing multiple ready to use liquids.

coloration process formulary may include the following: Chromium 2-Ethylhexanoate, Iron 2-Ethylhexanoate, Cobalt 2-Ethylhexanoate, Manganese 2-Ethylhexanoate, Copper 2-Ethylhexanoate, Zirconium Carboxylate, Yttrium Carboxylate, Zinc 2-Ethylhexanoate, D-Limonene: formula: C10H16 (natural) CAS #5989-27-5 TSCA; Soya Ester (Natural), Mineral Spirit (Petroleum HYdroCarbon).

For example, Coloring Material Ingredients may include: 6% Iron Hex-Cem Solution, 8% Chromium Hex-Cem, 24% Zirconium Hex-Cem, 6% Manganese Hex-Cem, 8% Nickel Hex-Cem, and/or 6% Cobalt Hex-Cem. Ingredients may also include CK D-Limonene Hydrocarbon.

A coloring system for dental ceramics may include may include, among other items, a series of color compositions FIG. 2, 200. In one example, the color compositions may be provided as ready-to-use color liquids, e.g., FIG. 2, 202, 204, 206, 208, 210, 212, 214, 216, 218, 220, 222, 224, 226, 228, 230. (In other examples, the color compositions may be provided in concentrates which are ready to use upon dilution.) The color liquids may be formulated to accommodate color adjustments along the wide range of incisal and gingival shades for color matching natural dentition represented by the reference numerals on the VITA shade guide. While the photograph has some color to it, the colors are not meant to be limiting. FIG. 2 merely illustrates an exemplary kit.

The technology may be supplied in a kit, for example, a kit that contains one of 5, 10, 15, 20, 25, 30, or more shades. The kit may also include a shade guide which is matched to the shades of the system. The kit may also include a thinner.

The formulary of the color liquids that are provided in the kit may include the following: a hydro carbon, Chromium 2-Ethylhexanoate, Iron 2-Ethylhexanoate, Cobalt 2-Ethylhexanoate, Manganese 2-Ethylhexanoate, Copper 2-Ethylhexanoate, Zirconium Carboxylate, Yttrium Carboxylate, Zinc 2-Ethylhexanoate, D-Limonene: formula: C10H16 (natural) CAS #5989-27-5 TSCA; Soya Ester (Natural), Mineral Spirit (Petroleum HYdroCarbon).

For example, Coloring Material Ingredients may include: 6% Iron Hex-Cem Solution, 8% Chromium Hex-Cem, 24% Zirconium Hex-Cem, 6% Manganese Hex-Cem, 8% Nickel Hex-Cem, and/or 6% Cobalt Hex-Cem. Ingredients may also include CK D-Limonene Hydrocarbon.

The following formulary chart provides an exemplary system, and kit of coloration liquids.

| | |
|---|---|
| A1 shift B1 (210) | Fe: —%, Cu: 0.05%, Mn (2%): 1.3% |
| A1 Shift A2 (202) | Fe: 2%, Co: 0.03% |
| A2 Shift A3 (204) | Fe: 2%, Co: 0.05%, Ni: 0.05% |
| A2 Shift A3.5 (206) | Fe: 4%, Co: 0.08% |
| A2 Shift A4 (208) | Fe: 8%, Co: 0.12%, Ni: 0.4%, Mn 2%: 1% |
| A2 Shift B2 (212) | Fe: 1%, Cu: 0.08% |
| A2 Shift B3 (214) | Fe: 5%, Cu: 0.1% |
| A2 Shift B4 (216) | Fe: 8%, Cu: 0.12%, |
| A2 Shift C1 (218) | Cu: 0.1%, Mn (2%): 2% |
| A2 Shift C2 (220) | Fe: 4% Ni: 0.1%, Cu: 0.1% Mn 2%: 5% |

-continued

| | |
|---|---|
| A2 Shift C3 (222) | Fe: 4%, Cu: 0.11%, Mn(2%): 7% Ni: 0.3% |
| A2 Shift C4 (224) | Fe: 6%, Ni: 0.6%, Cu: 0.12%, Mn 2%: 9% |
| A2 Shift D2 (226) | Fe: —%, Ni: 0.45%, Cu: 015%, Mn (2%): 4% |
| A2 Shift D3 (228) | Fe: 2%, Ni: 0.2%, Co: 0.15%, Mn(2%): 1% |
| A2 Shift D4 (230) | Fe: 2%, Ni: 0.5%, Cu: 0.23%, Mn(2%): 3.2% |

Measured by weight. It should be understood that each of the coloring liquids may be sold separately or may be sold in kits in various arrangements. All of the liquids listed above do not have to be sold together. Also, each must be sold separately, e.g., to accommodate replacements and/or to accommodate individual selection and needs.

The balance of the color liquid may include the following: hydrocarbon, Chromium 2-Ethylhexanoate, Iron 2-Ethylhexanoate, Cobalt 2-Ethylhexanoate, Manganese 2-Ethylhexanoate, Copper 2-Ethylhexanoate, Zirconium Carboxylate, Yttrium Carboxylate, Zinc 2-Ethylhexanoate, D-Limonene: formula: C10H16 (natural) CAS #5989-27-5 TSCA; Soya Ester (Natural), Mineral Spirit (Petroleum HYdroCarbon).

For example, Coloring Material Ingredients may include: 6% Iron Hex-Cem Solution, 8% Chromium Hex-Cem, 24% Zirconium Hex-Cem, 6% Manganese Hex-Cem, 8% Nickel Hex-Cem, and/or 6% Cobalt Hex-Cem. Ingredients may also include CK D-Limonene Hydrocarbon.

The liquid composition may not use water or alcohol as a solvent. Rather, the liquid composition may use hydrocarbon as a solvent.

Use of the disclosed coloring system may allow for prosthesis, crowns, and restorations that measure less than 0.5 mm in thickness. They may further create translucence and natural color matching on a "contact lens" thickness of restoration material.

Commonly, it is understood that no dyes will adhere to Zirconium/yttrium ceramics due to the strength of the material. All currently marketed dye solutions rely upon applications during the pre-sintered or absorbent stage of the material. The dyes that are currently available are 02 sensitive and they are also degraded rapidly at temperatures over 900° C. Surprisingly, the disclosed compositions and systems bond to the Zirconium/yttrium restoration at temperatures over 900° C. without losing pigment. Fluorescence may be added to make the tooth look more natural. For example, fluorescence may be added with down to 0.01% glassy ceramic. Furthermore, while in the knowledge of the art, ceramic does not bond to Zirconium, it has been demonstrated that use of the disclosed liquid colorant compositions bonds the glassy ceramic layer to Zirconium.

Post Sintering Color Correction

Often, although the practitioner performed careful color matching, and started with a carefully selected colored block, the final restoration does not provide the appropriate natural appearance and does not blend in with the natural denature.

It is thought in the art that post-sintering coloration of zirconium is impossible. Therefore, it was a unique and surprising result that with the disclosed system, even zirconium restorations may be color adjusted after sintering. The ready to use liquids of the method, system, and kit allow for high temperature zirconia/porcelain color modification. The color liquids and available in a wide range of colors and allow formulation of most tooth and tissue shades straight from the bottle with fidelity.

Another surprising result is that, with the post-sintering coloration system and compositions disclosed herein, there is no need to sandblast the post-sintered restoration. The disclosed coloration system bonds even to the smoothest of zirconia surfaces and laminating porcelain chemically bonds to the disclosed coloration system of stains.

The post-sintering coloration stains disclosed herein chemically bond to sintered zirconia after backing. The coloration system or stains may be supplied as a series of color liquids, such as a kit, see for example FIG. 2.

We disclose a system, method, and kit for coloring dental ceramics which includes at least one coloring liquid capable of adjusting the shade of a dental restoration milled from a colored zirconia porcelain block from one color value of the VITA shade guide to a different color value of the VITA shade guide. A few non-limiting examples follow. In one example, a kit may include a coloring liquid that is capable of adjusting the color of an dental restoration milled from an A1 colored block (a block or blank having a shade that matches the A1 value on the VITA shade guide) to a different color value of the VITA shade guide, including but not limited to A2, A3, A3.5, A4, B1, B2, B3, B4, C1, C2, C3, C4, D2, D3, D4. The color adjustment is predictable. The color adjustment is performed by a simple dipping and is complete and ready to fire (after removing excess) within about 5 to about 10 seconds. In a second example, a kit may include a coloring liquid that is capable of adjusting the color of an dental restoration milled from an A2 colored block (a block or blank having a shade that matches the A1 value on the VITA shade guide) to a different color value of the VITA shade guide, including but not limited to A3, A3.5, A4, B1, B2, B3, B4, C1, C2, C3, C4, D2, D3, D4. The color adjustment is predictable. The color adjustment is performed by a simple dipping and is complete and ready to fire (after removing excess) within about 5 to about 10 seconds. In a third example, a kit may include a coloring liquid that is capable of adjusting the color of an dental restoration milled from an A3 colored block (a block or blank having a shade that matches the A1 value on the VITA shade guide) to a different color value of the VITA shade guide, including but not limited to A3.5, A4, B1, B2, B3, B4, C1, C2, C3, C4, D2, D3, D4. The color adjustment is predictable. The color adjustment is performed by a simple dipping and is complete and ready to fire (after removing excess) within about 5 to about 10 seconds. A "color value of the VITA shade guide" refers to any of the designations used in that guide, e.g., A1, A2, A3, A3.5, A4, B1, B2, B3, B4, C1, C2, C3, C4, D2, D3, D4, Incisal Light, Incisal Dark, Occlusal, and Pink. The predictable result is demonstrated by FIG. 1. Turning to FIG. 1, the top line of teeth represent the VITA shade guide 102. The bottom row 104 demonstrates the fidelity of color that can be achieved with one dip using the disclosed coloring liquids.

While the foregoing written description of the invention enables one of ordinary skill to make and use what is considered presently to be the best mode thereof, those of ordinary skill will understand and appreciate the existence of variations, combinations, and equivalents of the specific exemplary embodiment and method herein. The invention should therefore not be limited by the above described embodiment and method, but by all embodiments and methods within the scope and spirit of the invention as claimed.

The invention claimed is:
1. A kit for coloring dental ceramics which comprises:
at least one coloring liquid;
the at least one coloring liquid capable of adjusting the shade of a dental restoration milled from a colored zirconia porcelain block from one color value of the VITA shade guide to a different color value of the VITA shade guide;

the at least one coloring liquid comprising:

a coloring liquid capable of adjusting the shade of a dental restoration from a VITA shade guide value of A2 to a VITA shade guide value of A3;

a coloring liquid capable of adjusting the shade of a dental restoration from a VITA shade guide value of A2 to a VITA shade guide value of A3.5;

a coloring liquid capable of adjusting the shade of a dental restoration from a VITA shade guide value of A2 to a VITA shade guide value of A4;

a coloring liquid capable of adjusting the shade of a dental restoration from a VITA shade guide value of A1 to a VITA shade guide value of A2; and a coloring liquid capable of adjusting the shade of a dental restoration from a VITA shade guide value of A1 to a VITA shade guide value of B1;

and the kit further comprising a coloring liquid comprising by weight Cu: 0.05% and Mn(2%): 1.3%;

and wherein a predictable color adjustment occurs in less than ten seconds.

2. The kit of claim 1, further comprising:
a coloring liquid comprising by weight Fe: 2% and Co: 0.03%.

3. The kit of claim 2, further comprising:
a coloring liquid comprising by weight Fe: 2%, Co: 0.05%, Ni: 0.05%; a coloring liquid comprising by weight Fe: 4%, Co: 0.08%.

4. The kit of claim 3, further comprising:
a coloring liquid comprising by weight Fe: 8%, Co: 0.12%, Ni: 0.4%, Mn(2%): 1%.

5. The kit of claim 4, further comprising:
a coloring liquid comprising by weight Fe: 1%, Cu: 0.08%.

6. The kit of claim 5, further comprising:
a coloring liquid comprising by weight Fe: 5%, Cu: 0.1%.

7. The kit of claim 6, further comprising:
a coloring liquid comprising by weight Fe: 8%, Cu: 0.12%.

8. The kit of claim 7, further comprising:
a coloring liquid comprising by weight Cu: 0.1%, Mn (2%): 2%.

9. The kit of claim 8, further comprising:
a coloring liquid comprising by weight Fe: 4% Ni: 0.1%, Cu: 0.1% Mn 2%: 5%.

10. The kit of claim 9, further comprising:
a coloring liquid comprising by weight Fe: 4%, Cu: 0.11%, Mn(2%): 7% Ni: 0.3%.

11. The kit of claim 10, further comprising:
a coloring liquid comprising by weight Fe: 6%, Ni: 0.6%, Cu: 0.12%, Mn(2%): 9%; and
a coloring liquid comprising by weight Ni: 0.45%, Cu: 015%, Mn (2%): 4%.

12. The kit of claim 11, further comprising:
a coloring liquid comprising by weight Fe: 2%, Ni: 0.2%, Co: 0.15%, Mn(2%): 1%.

13. The kit of claim 12, further comprising:
a coloring liquid comprising by weight Fe: 2%, Ni: 0.5%, Cu: 0.23%, Mn(2%): 3.2%.

14. The kit of claim 1, further comprising:
a coloring liquid comprising by weight Cu: 0.05% and Mn(2%): 1.3%;
a coloring liquid comprising by weight Fe: 2% and Co: 0.03%;
a coloring liquid comprising by weight Fe: 2%, Co: 0.05%, Ni: 0.05%; a coloring liquid comprising by weight Fe: 4%, Co: 0.08%;
a coloring liquid comprising by weight Fe: 8%, Co: 0.12%, Ni: 0.4%, Mn(2%): 1%;
a coloring liquid comprising by weight Fe: 1%, Cu: 0.08%;
a coloring liquid comprising by weight Fe: 5%, Cu: 0.1%;
a coloring liquid comprising by weight Fe: 8%, Cu: 0.12%;
a coloring liquid comprising by weight Cu: 0.1%, Mn (2%): 2%;
a coloring liquid comprising by weight Fe: 4% Ni: 0.1%, Cu: 0.1%, Mn 2%: 5%;
a coloring liquid comprising by weight Fe: 4%, Cu: 0.11%, Mn(2%): 7% Ni: 0.3%;
a coloring liquid comprising by weight Fe: 6%, Ni: 0.6%, Cu: 0.12%, Mn(2%): 9%;
a coloring liquid comprising by weight Ni: 0.45%, Cu: 015%, Mn (2%): 4%;
a coloring liquid comprising by weight Fe: 2%, Ni: 0.2%, Co: 0.15%, Mn(2%): 1%; and
a coloring liquid comprising by weight Fe: 2%, Ni: 0.5%, Cu: 0.23%, Mn(2%): 3.2%.

* * * * *